United States Patent [19]
Konotchick

[11] Patent Number: 5,499,013
[45] Date of Patent: Mar. 12, 1996

[54] PULSE POWER GENERATOR

[76] Inventor: John A. Konotchick, 3116 Mercer La., San Diego, Calif. 92122

[21] Appl. No.: 238,160

[22] Filed: May 4, 1994

Related U.S. Application Data

[63] Continuation-in-part of Ser. No. 851,068, Mar. 13, 1992, abandoned.

[51] Int. Cl.$^6$ .............................. G08B 1/08; G08B 13/08
[52] U.S. Cl. .......................... 340/539; 340/541; 340/545; 340/547; 340/693
[58] Field of Search ................................... 340/539, 541, 340/545, 547, 693

[56] References Cited

U.S. PATENT DOCUMENTS

| | | | |
|---|---|---|---|
| 3,772,669 | 11/1973 | Johnston et al. | 340/539 |
| 3,781,836 | 12/1973 | Kruper | 340/539 |
| 3,818,467 | 6/1974 | Willis | 340/539 |

Primary Examiner—Donnie L. Crosland
Attorney, Agent, or Firm—John R. Ross

[57] ABSTRACT

A mechanical to electrical pulse power generator. Powerful rare-earth magnets (e.g., Neodymium-Iron-Boron, or Samarium-Cobalt) create strong flux fields. These flux fields are used to produce large percent change in flux through a coil of wire upon the triggering of triggering mechanisms which causes a snap action to assure creation of an electrical pulse sufficient to activate an alarm. A mechanical force in a first direction will cause a jerk action which will produce a pulse shape identifiable to the first direction force and a mechanical force in a second direction will produce a different jerk action which will produce a pulse shape identifiable to the second direction force. Low power electronics use the energy in these pulses to activate a radio frequency transmitter to transmit a signal revealing the direction of the mechanical force. A preferred embodiment codes the transmitter signal to indicate the source of the signal.

13 Claims, 10 Drawing Sheets

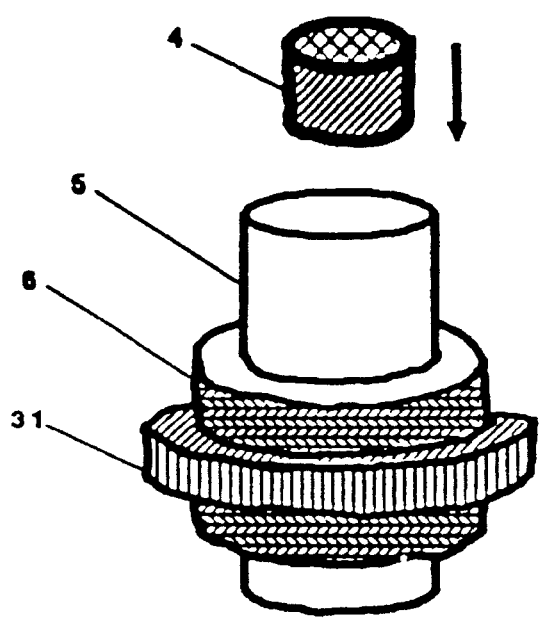
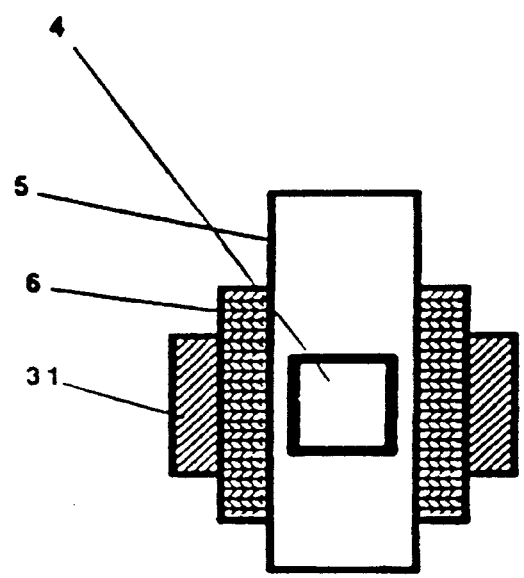
FIG. 5A
FIG. 5B

PULSE POWER GENERATOR

This application is a continuation-in-part application of Ser. No. 07/851,068, filed Mar. 13, 1992, now abandoned. This invention relates to pulse power generation and is particular to such generation powered by mechanical energy.

BACKGROUND OF THE INVENTION

There have been a great many attempts at developing devices to provide short pulses of electrical power using mechanical energy. Such devices would be useful for powering equipment such as intrusion alarms where the intruder would provide the mechanical energy to produce the electrical power.

Intrusion alarms and sensors are normally wired to electrical power lines and the outputs are transmitted by electrical conduction to control stations. One alternative, especially used in remote locations, has been to use batteries to power radio frequency transmitters to transmit an alarm signal to a control station. Battery replacement can become a problem.

U.S. Pat. Nos. 3,772,669 and 3,831,157 describe methods attempted to develop pulse power for alarm use. Both patents require large forces (over 15 lbs) to activate them; both are extremely limited in applications (require high leverage, essentially nonconductive door jams), neither has envisioned the need for an alarm encoding to indicate alarm location in a multiple alarm environment, neither is capable of providing bi-directional outputs (i.e., "alarmed" position, and "activated" position), and neither is capable of providing easy application to other uses.

U.S. Pat. Nos. 4,020,369 and 4,118,717, use flux switching to generate electrical pulses for camera use. Both use an inefficient design for generating useful energy. They wrap the induction coil only around one pole piece of the magnet, and use only one polarity sense of the induced voltage. The coil on the pole piece loses efficiency due to all the flux loss paths surrounding the magnet. This design would not be appropriate for intrusion alarm use, even if it were scaled up in energy output, because of the large attractive force which would be required to pull the keeper away from the magnet.

U.S. Pat. Nos. 4,412,355 and 4,480,808 use magnets oscillating past pole pieces containing a coil to generate energy from mechanical inputs. The power being produced will be roughly a sinusoid of frequency corresponding to the oscillations of the magnets. Neither device would provide electrical pulses appropriate for intrusion alarm use.

To effectively operate a wireless intrusion alarm an electrical pulse should provide a peak power of at least 0.1 Watt to provide sufficient RF prime power, and should have a duration of at least 30 milliseconds to provide sufficient time to code the transmission, with a total energy of at least 3 millijoules.

OBJECTIVES

What is needed is a device which can generate electrical power in excess of 0.1 Watts for over 30 milliseconds, that can indicate both "armed" and "alarmed" status of the device, that has a "snap" action to produce repeatable energy pulses that cannot be defeated by very gradual door or window opening, that can provide a means of discriminating individual alarms in a multiple alarm environment, that is easily adaptable to various working voltages and alarm installations, that requires little force to trigger it, and that is small, simple, and efficient.

Accordingly, it is the objective of this invention to provide a device which can be driven by the opening or closing of a door, window, or other portal. A further objective is to use the energy in the pulse to generate a coded radio signal which can be detected at a control station.

SUMMARY OF THE INVENTION

The present invention provides a mechanical to electrical pulse power generator. Powerful rare-earth magnets (e.g., Neodymium-Iron-Boron, or Samarium-Cobalt) create strong flux fields. These flux fields are used to produce large percent change in flux through a coil of wire upon the triggering of triggering mechanisms which causes a snap action to assure creation of an electrical pulse sufficient to activate an alarm. A mechanical force in a first direction will cause a jerk action which will produce a pulse shape identifiable to the first direction force and a mechanical force in a second direction will produce a different jerk action which will produce a pulse shape identifiable to the second direction force. Low power electronics use the energy in these pulses to activate a radio frequency transmitter to transmit a signal revealing the direction of the mechanical force. A preferred embodiment codes the transmitter signal to indicate the source of the signal.

BRIEF DESCRIPTION OF THE DRAWINGS

FIG. 5A Is an expanded view of another embodiment of a magnet-through-coil pulse power generator.

FIG. 5B is a cross section view of FIG. 5A with the magnet in the center of the coil.

DESCRIPTION OF PREFERRED EMBODIMENTS

A preferred embodiment of the present invention for producing battery-less electrical power for intrusion alarms is described by reference to FIG. 1A. This embodiment uses some of the mechanical energy involved in the opening or closing of a window or door to power a coded radio-frequency transmitter. The radio-frequency coded signal is then processed by a receiving station which decodes the signal to identify the particular alarm which was activated. This embodiment permits easy installation of a wireless, battery-less, alarm system.

Figure 1A:
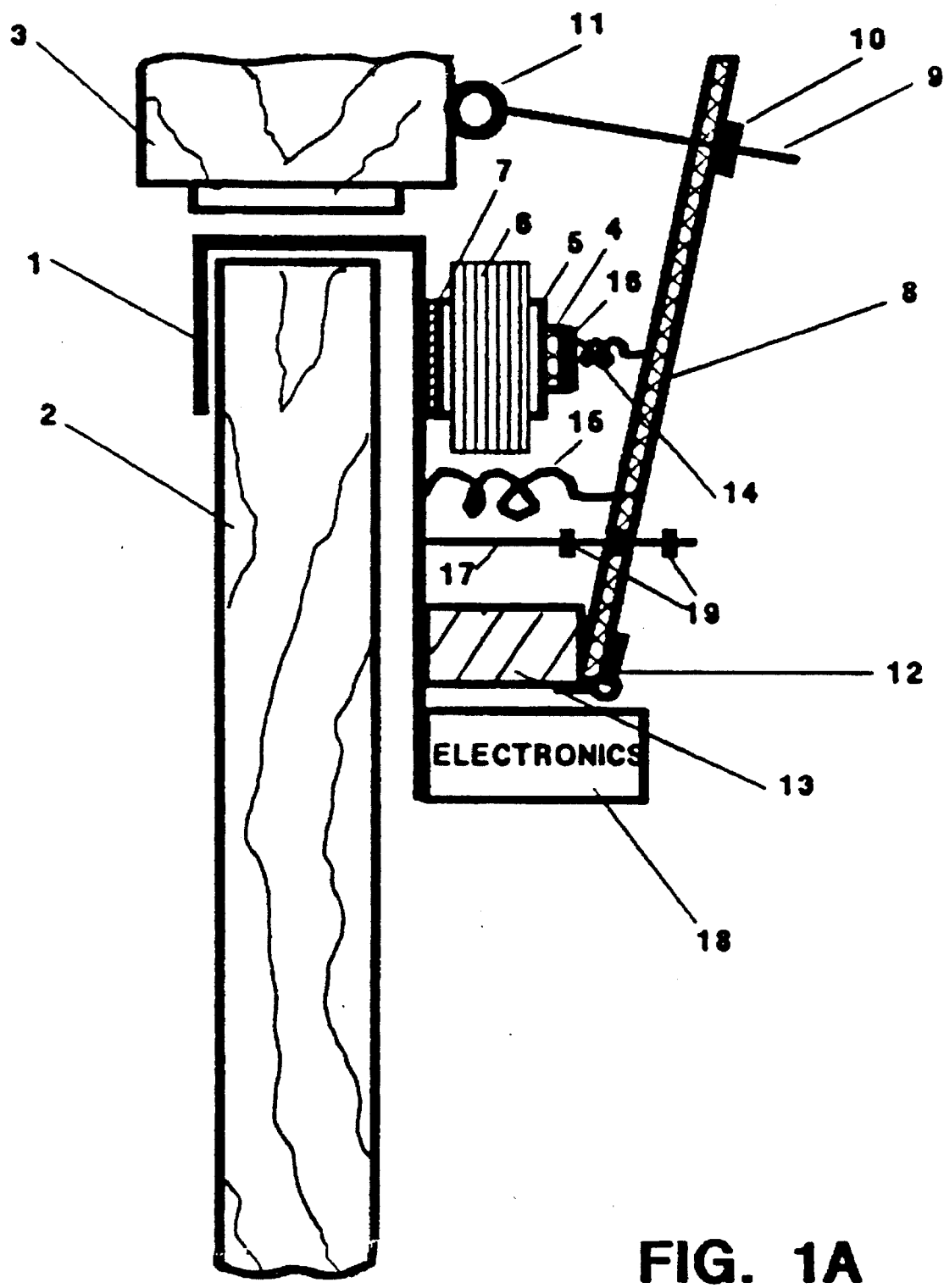
FIG. 1A is an illustration of one embodiment of the pulse power generator, shown attached to the top of a door.

FIG. 1A illustrates a preferred embodiment as a battery-less door alarm. A ferrous bracket 1 attaches the alarm unit to the top of a door 2. Bracket 1 is comprised of ⅛ inch thick by 2 inch wide steel. Bracket 1 being magnetically permeable metal, will attract magnet 4 when in close proximity to it. A 1-inch, brass hinge 12 was used to attach a ¹⁄₁₆ inch thick by 1 inch wide brass lever arm 8 to a support member 13. A coil spring 14 was used to attach the brass lever arm 8 to the magnet. The attachment to the magnet was by attaching the spring 14 to a ¼ inch thick, 1 inch diameter disk of steel 16 which used magnetic attraction to connect to magnet 4. A cushion 7 of non-ferrous, non-conductive material is used between the magnet, and the bracket 1 to both cushion the magnet impact, and also to vary the "jerk" and pull-away force required to arm the device.

The mechanism is mounted on the inside (an inward opening door is shown) of the door. Magnet 4 is a powerful rare-earth, permanent magnet and slides within a non-ferrous, non-conductive, thin tube 5 which is wrapped on the outside with a coil of magnet wire 6. In one prototype model built and tested by the applicant, this magnet 4 was a cylindrical Nd magnet with a thickness of 0.375 inches in the direction of magnetization, and a diameter of 1 inch. The magnet can be obtained from Magnet Sales and Manufacturing Co., Inc. (model # 28DNE6424). This magnet has a maximum energy product ($BH_{max}$) of 28 million Gauss Oersteds. Coil 6 was comprised of 8,500 turns of #38 AWG magnet wire, with an inside diameter of 1,127 inches, and an outside diameter of about 2.0 inches. It was about ½ inches wide, and had a resistance of 2,216 ohms.

By making the cushion 7 thin, a strong "snap" or "jerk" will result when the door is opened or closed, and a force will be required to pull the magnet away from the bracket 1. By increasing the thickness of cushion 7 this pull-away force can be reduced, but the jerk action is also diminished. A piece of ¼ inch thick foam pad was used in the model described.

The spring 14 helps to provide the flexibility required to permit the magnet to both "jerk" toward the bracket 1 and to "jerk" away, to give a standard output voltage from coil 6 regardless of the speed at which the door is opened or closed. An adjustable arm 9 is threaded through a locknut 10 so the length of arm 9 can be adjusted. A padded foot 11 contacts the door frame 3. This adjustable arm 9 permits adaptation to various sizes of upper door frame 3 thicknesses. The adjustment is made so that when the door is closed, the magnet 4 will be pulled outside of coil 6 but not outside of tube 5. A steel rod 17 threaded with 8-32 threads is connected to limit the maximum movement of lever arm 8 to prevent pulling magnet 4 out of the cylinder 5. It has lock nuts 19 adjustable to limit the range of movement of the lever arm 8.

A second two inch long spring 15 is used to pull the brass lever arm toward the door 2 when the door is opened. This will cause the magnet to enter the tube 5 and to be attracted by the bracket 1. This attraction will "jerk" the magnet 4 against the cushion 7 and cause it to come to rest within the coil 6 having generated a voltage in coil 6 in the process.

Similarly, when the door is closed, the lever arm 8 will create a force trying to pull the magnet 4 away from the bracket 1 and cushion 7. At a certain force, this will "jerk" the magnet 4 away, and generate an opposite polarity voltage pulse in coil 6. The voltage produced in coil 6 goes to power the electronics package 18 which contains a radio frequency transmitter.

Figure 3A:
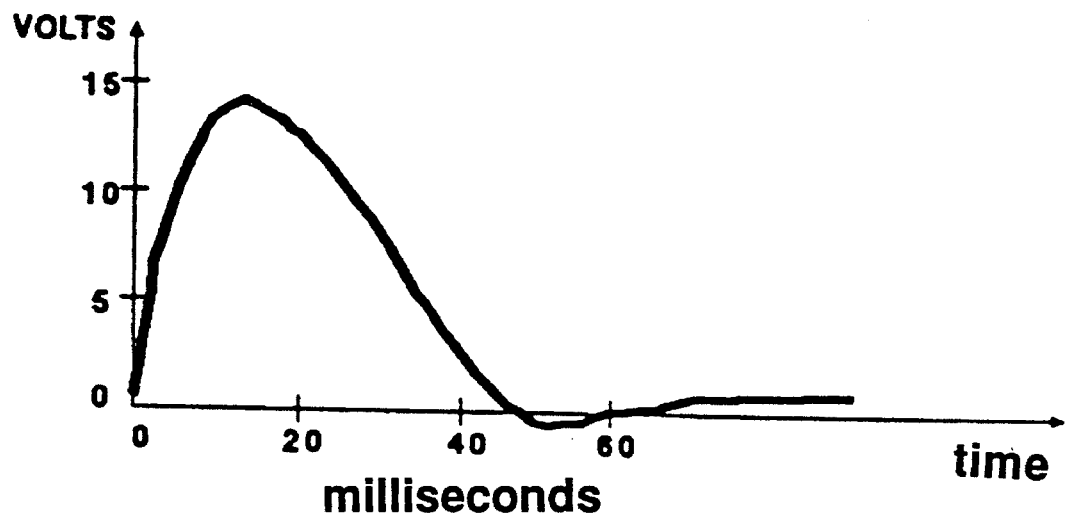
FIG. 3A is a voltage response to closing the door.
Figure 3B:
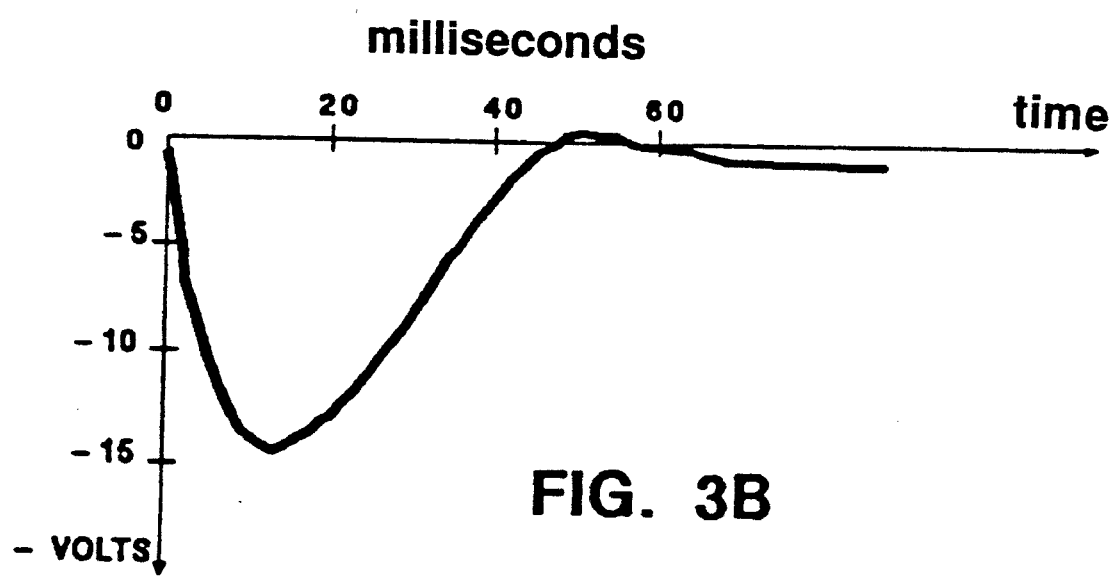
FIG. 3B is a voltage response to opening the door.

Applicant has produced prototype devices similar to that shown in FIG. 1 which generated over 2.5 Watts of peak power for a duration of about 20 milliseconds, but for the model described above the output voltage was about 15 volts across a load resistor of 2,200 ohms, providing about 0.1 Watts for about 40 milliseconds on both opening and closing the door. FIG. 3A shows the shape of the voltage created, as a function of time, on a 2,200 ohm load resistor when the door is closed. FIG. 3B shows the voltage shape created when the door is opened.

Figure 7:
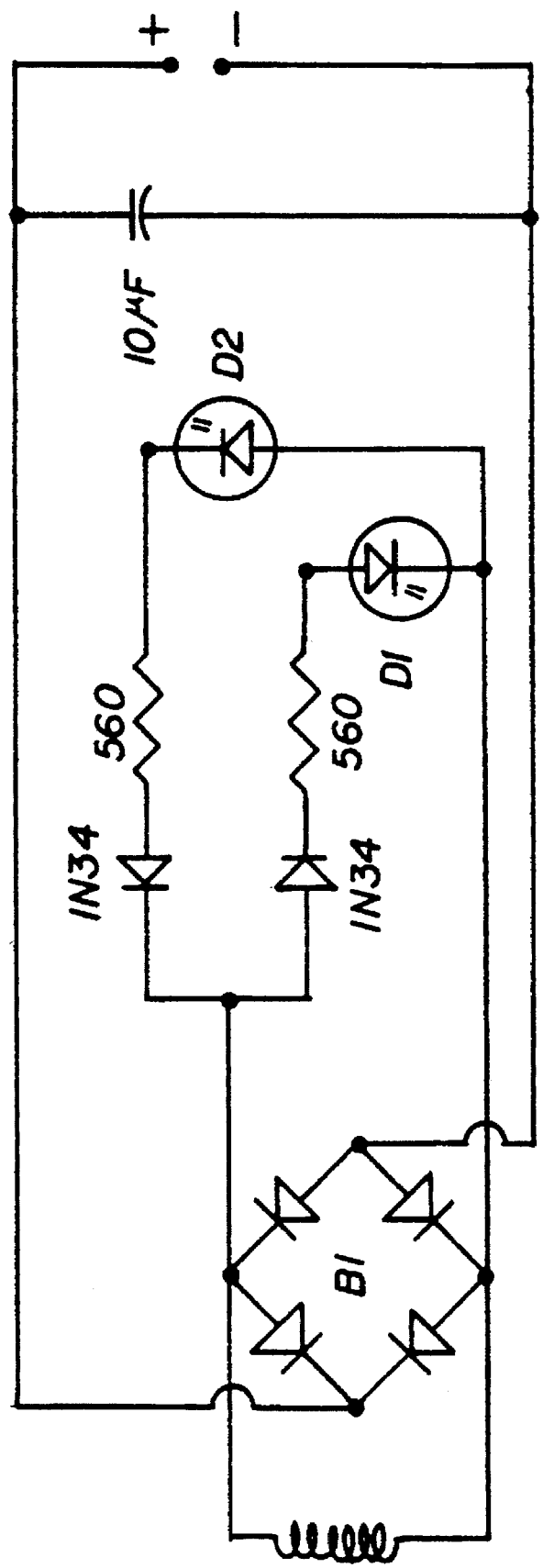
FIG. 7 is a simple circuit that indicates whether the door was opened or closed, and that stores pulse energy on a capacitor.

To provide a demonstration of the device in operation, simple test circuits as shown in FIG. 7 were used. The circuit shown in FIG. 7 would flash D1, the "green" light-emitting-diode (LED) when the door was closed, and would flash D2, the "red" LED when the door was opened. A 10-microFarad capacitor, C1, would be charged to about 10 volts when the door was opened or closed.

HOW WE MAKE AN ALARM

Figure 1C:
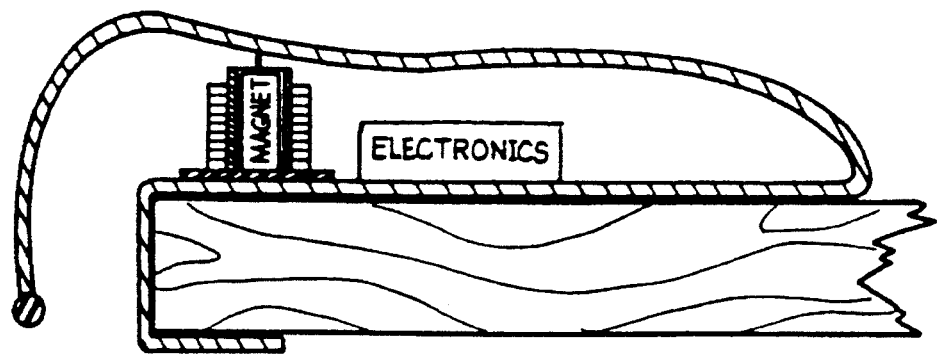
FIG. 1C is a view of the FIG. 1B version with the door opened.
Figure 1B:
FIG. 1B is a simplified version of the embodiment shown in FIG. 1A with the door in a closed position.
Figure 1B:
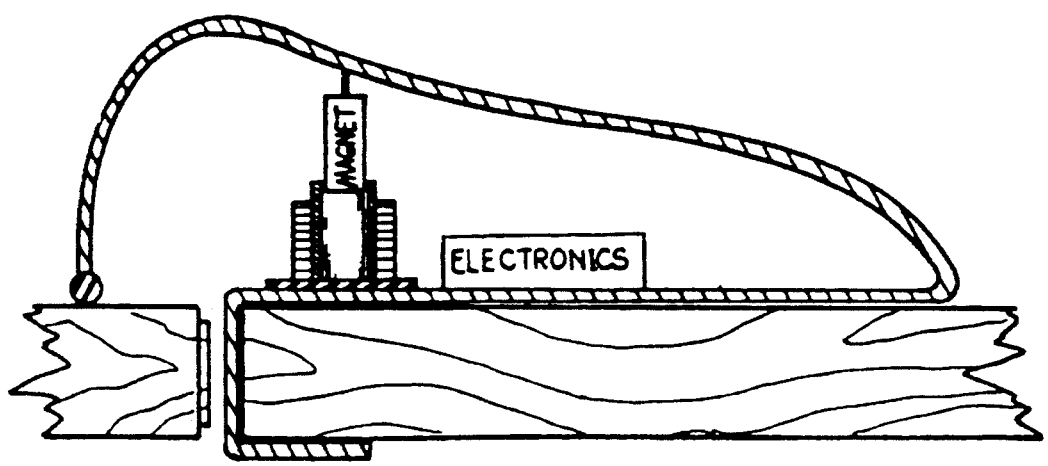
Figure 2:
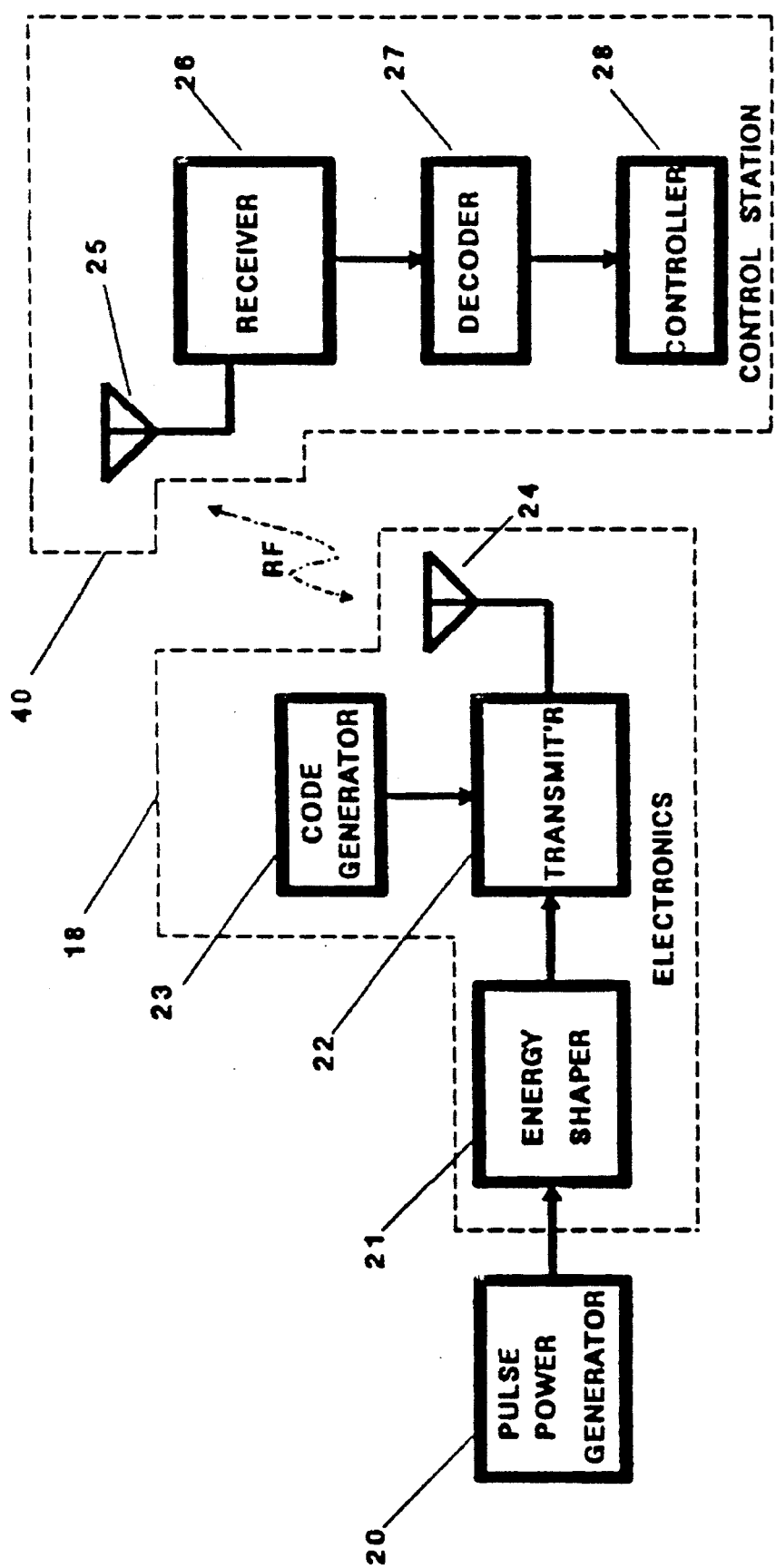
FIG. 2 is a block diagram showing the various elements involved in my battery-less intrusion alarm.

FIG. 2 is a block diagram of a preferred application for this preferred embodiment. The elements of FIG. 1, except the electronics package 18 comprise the electrical pulse generator. These elements are contained in the box called pulse generator 20 in FIG. 2. The output of pulse generator 20 will be a single polarity pulse with a peak of about 0.1 Watts with a duration of about 40 milliseconds as shown in FIGS. 3A and 3B. It could be made with a peak pulse power in excess of 10 Watts, however, if desired. The single polarity will be either positive or negative, depending upon whether the generator was triggered by a door opening or closure.

Energy shaper 21 uses a polarity indicating circuit to supply the code generator 23 with this information, and components to adapt the generated pulse to the power needs of the transmitter 22 and the code generator 23. For some applications long voltage durations are desired, so energy shaper 21 also has provision to provide a buffered voltage to the radio frequency transmitter 22. A bridge rectifier assembly followed by a 10 microFarad capacitor in parallel as in FIG. 7 could be used as the energy shaper 21. This energy shaper 21 could also use a voltage regulator circuit to provide more constant voltage supply for other applications.

Figure 8:
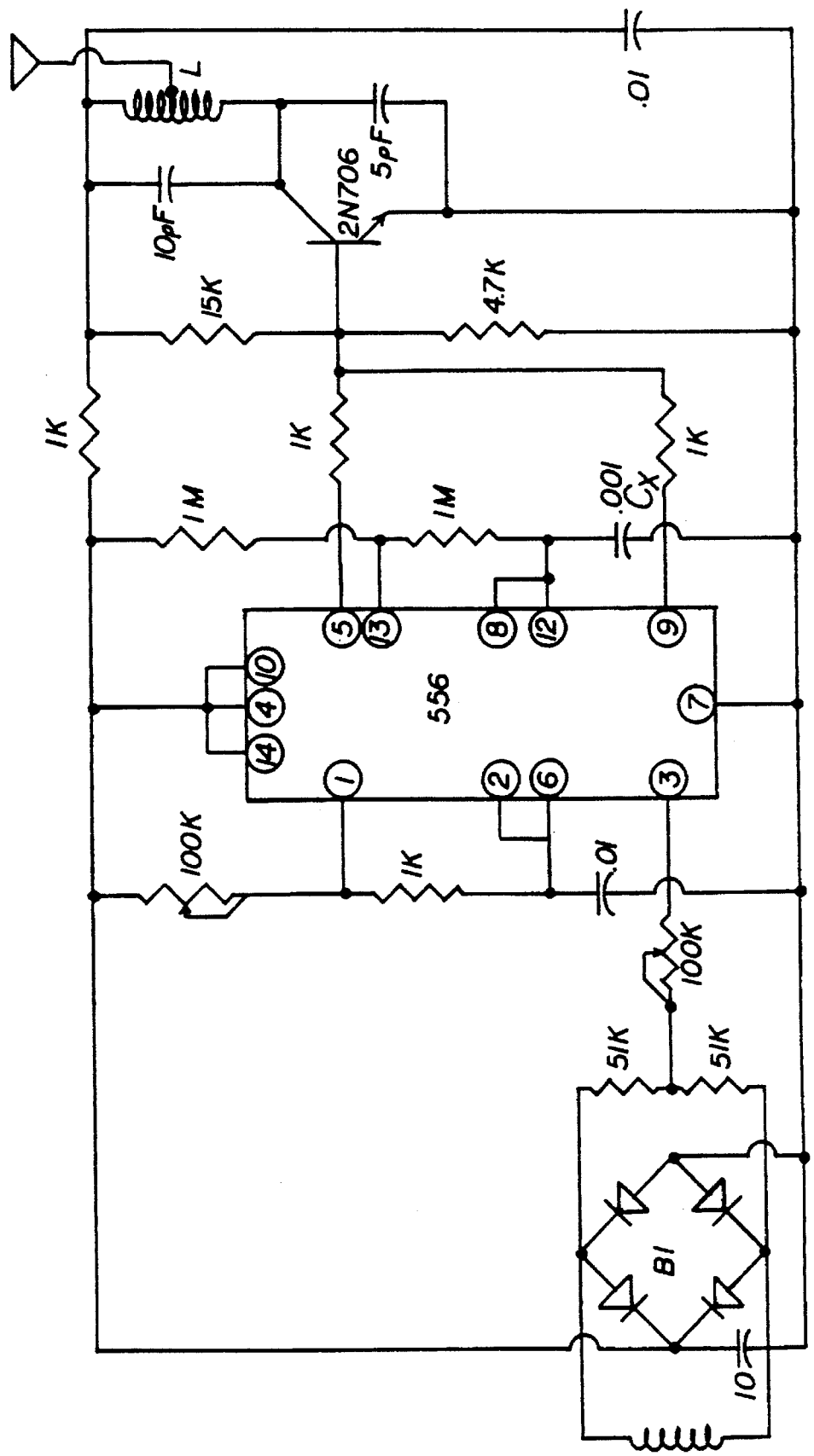
FIG. 8 is an electrical schematic of the elements comprising an embodiment of the battery-less door alarm.

The code generator 23 provides an information code to modulate the radio frequency signal from the transmitter 22. This code would be used to indicate whether the alarm was "armed" (door closed) or "alarmed" (door opened), and to identify which particular alarm was sending the signal. A Radio Shack 556 integrated circuit was used to design a prototype of this coder, using the voltage controlled oscillator circuit on page 15 of Radio Shack's "Engineer's Mini-Notebook" (stock number 276-5010) to indicate closing or opening by up or down shift of frequency, and the astable oscillator circuit on page 7 of the same text to provide a frequency indicating the particular device. The two coded signals from the 556 integrated circuit were then combined and fed into an FM transmitter of the type shown on page 683 of Volume 3, "Encyclopedia of Electronic Circuits", by Rudolf Graf. The signal from transmitter 22 is transmitted through transmitter antenna 24 to receiver antenna 25 located at control station 40. FIG. 8 illustrates an electrical schematic of this design. The pulse polarity will be used on pin #3 of the 556 integrated circuit to sweep a frequency either up or down in frequency corresponding to pulse polarity. This swept frequency will exit on pin #5. The capacitor $C_x$ will determine the fixed frequency which exits at pin #9 to provide the unique sensor identification. The coil $L_1$ is 4 turns of #20 enameled wire, airwound, 0.25 inch diameter, by 0.2 inch long, center tapped. The antenna is an 18 inch long wire. This will provide an FM transmission detectable over several hundred yards.

Control station 40 has receiver 26 which decodes the received signal in a decoder 27 and sends the decoded information to the controller 28. For this prototype a commercial FM receiver could be used with the voice output being displayed on an oscilloscope, chart recorder, or spectrum analyzer to decode the signals. The controller could be a person that uses the information to make an appropriate response to the alarm signal.

In our commercial model we plan to use a much more sophisticated coder, transmitter and receiver/controller. The transmitter could be an integrated circuit chip, such as the Motorola MC2833, the receiver could also be an IC chip, such as the Motorola MC3367 FM Receiver. The coding/decoding could use a chip used for paging systems, such as the MX013 HSC Tone Decoder from Metropage. The receiver/controller will be designed to assign weights to a variety of complementary alarm inputs to reduce false alarms, and to also provide a variety of appropriate responses.

MOVING MAGNET PULSE GENERATOR

Figure 4A:
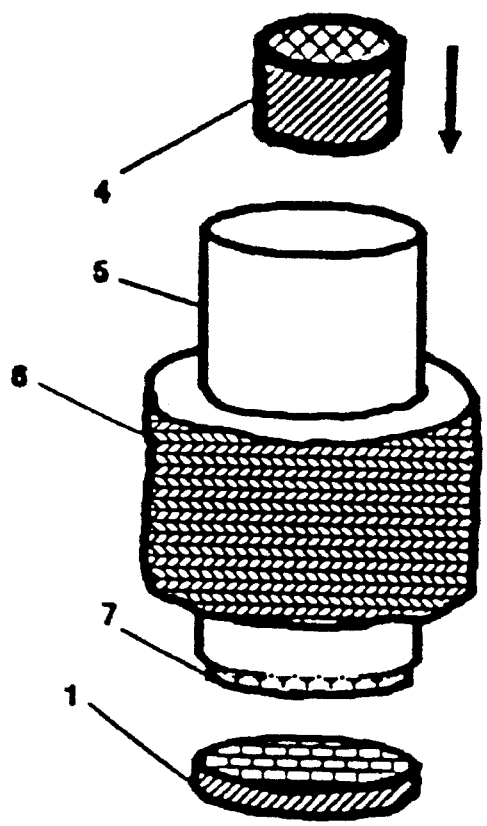
FIG. 4A is an expanded view of the active elements of the pulse generator used in FIG. 1.
Figure 4B:
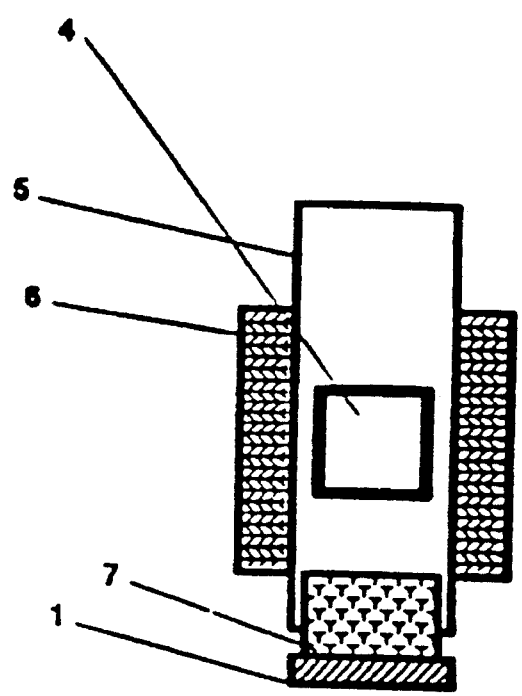
FIG. 4B is a cross section view of FIG. 4A with the magnet in the center of the coil.

FIGS. 4A and 4B show the active parts of the pulse power generator. They consist of magnet 4, non-conductive tube 5, coil of magnet wire 6, attracting permeable metal 1, and cushioning spacer 7.

The magnet 4 should be slightly smaller in diameter than the thin tube 5 to permit easy movement of magnet 4 within tube 5. For greater efficiency, the distance between magnet 4 and coil 5 should be as small as practical. The voltage generated in coil 6 by this device is, by Faraday's Law, equal to $N(d\phi/dt)$, where "N" is the number of turns in coil 6 that experience the flux change of $d\phi/dt$.

The magnet 4 provides the flux, $\phi$, and its movement through the tube 5 and coil 6 provides the change with time. On entering the coil 6 the magnet 4 generates a rise in flux, producing a voltage of one polarity. Upon exiting the coil 6 the magnet 4 reduces the flux in the opposite fashion, producing a voltage in the coil of the opposite polarity. The cushion 7 prevents the magnet from exiting the coil, from damaging itself on impact with the permeable metal, 1, and from creating too large an attractive force to overcome in withdrawing the magnet 4.

The flux from magnet 4 is strongest near the magnet, and diminishes away from the magnet depending upon its shape and dimensions. The coil 6 length and thickness can be matched to this flux path to improve efficiency. The coil wire size used will affect what voltage level will be generated for a particular coil size. In general, factors which increase the power output from this embodiment are an increase in magnet flux strength, an increase in coil size, an increase in speed through the coil of the magnet, a decrease in wire size, and a decrease in wire conductivity.

FIG. 5A and 5B show another embodiment of the pulse power generator. The permeable material at the end of the tube in FIG. 4A and 4B, 1, is moved to a ring 31 which is placed over the induction coil 6. Otherwise the models are the same. With the high permeability ring in this position, the magnet 4 is attracted to the center of the coil 6 where it comes to rest. This embodiment provides the same "jerk" of magnet 4 movement on both entry and exit from the coil.

FLUX SWITCHING PULSE GENERATOR

Figure 6A:
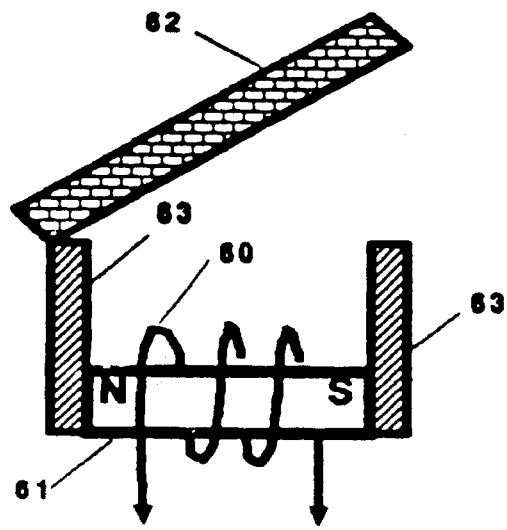
FIG. 6A is a flux-switching embodiment of a pulse power generator.
Figure 6B:
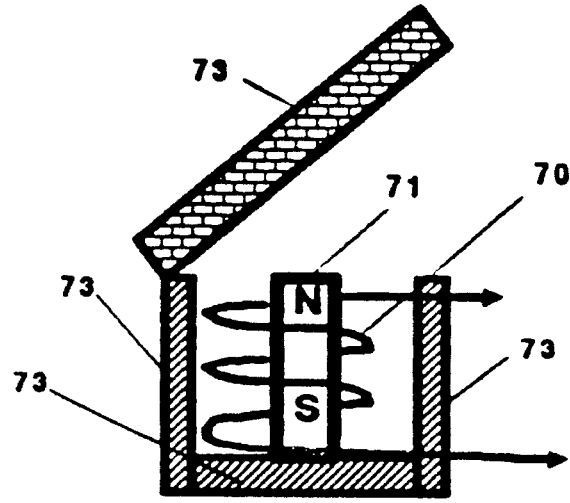
FIG. 6B is another flux-switching embodiment of a pulse power generator.
Figure 6C:
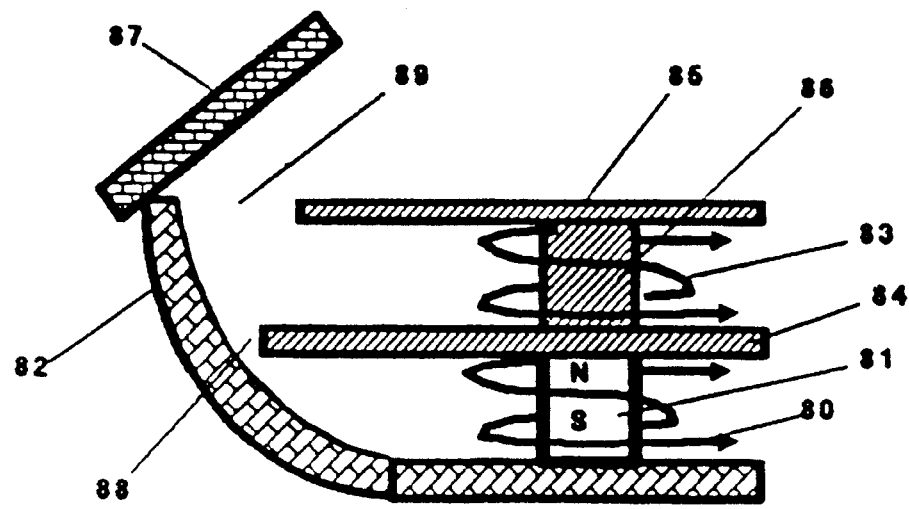
FIG. 6C is another flux-switching embodiment of a pulse power generator.

FIG. 6A, 6B, and 6C show three other embodiments of the pulse power generator. These embodiments rely upon flux-switching, rather than movement of a magnet through the coil. In FIG. 6A coil 60 is wrapped around magnet 61. With permeable keeper 62 off the pole pieces 63 a small amount of magnetic flux is flowing. With keeper 62 dropped on to pole pieces 63 a low reluctance path is created which greatly increases the flux flowing in this magnetic circuit. This generates a voltage of one polarity in coil 60. When keeper 62 is pulled off the pole pieces 63 an opposite voltage is developed in coil 60. This embodiment has the same properties as in FIGS. 4 and 5. That is, they provide polarity indications of "armed" and "alarmed", high power and energy, a "snap" when opened or closed, etc.

FIG. 6B shows another embodiment of a flux-switching pulse power generator. Again the coil 70 is wrapped around a magnet 71. With keeper 72 off pole pieces 73 little flux flows. With keeper 72 on the pole pieces 73 a low reluctance magnetic path is created, and flux flow greatly increases, generating a voltage of one polarity. The pole pieces 73 in this embodiment could be configured as a circular closed cylinder, similar to an electromagnet. This embodiment, again possesses the characteristics of the previous embodiments.

One of the possible shortcomings of flux-switching pulse power generators is the force required to make or break the magnetic circuit. For high power generation, FIGS. 6A and 6B would require considerable force to close and open the circuits. They also only use coils around the magnet, which is efficient, but provides limited coil volume unless very large magnets are used. The coils could also be wound around pole pieces, as is often done, but this usually results in considerable flux leakage losses, limiting the efficiency of power generation. One solution to these problems is shown in FIG. 6C.

FIG. 6C shows a side view of another flux-switching pulse power generator. This embodiment also has a strong magnet 81 with a coil 80 wrapped around it to generate a voltage. In addition it has a cylinder of high permeability material 86 around which is wound a second coil 83. Plate 84 of high permeability material is attached by magnetic attraction to magnet 81 and provides a medium reluctance magnetic path 88 through high permeability curved pole piece 82. This medium reluctance path 88 essentially shields upper elements 83, 85, and 86 from the flux flow with keeper 87 in the open position. The gap provided with the open keeper position 89 is much larger than gap 88. When keeper 87 is moved down onto pole piece 85 it creates a much lower reluctance path for the magnet 81 through pole pieces 84, 86, 85, and 82. This increased flux flow creates a voltage of one polarity in coils 80, and 83. When keeper 87 is pulled away from pole piece 85 the opposite polarity voltage will be generated, as the flux path again diminishes to the leakage through gap, 88. With this embodiment, the gap 89 can be made relatively small in comparison to the length of keeper 87 to diminish the force required to make or break the magnetic flux circuit. The embodiment also allows the addition of coil 83 to be used to generate additional power.

OTHER EMBODIMENTS

A variety of different mechanical arrangements can be used to adapt the pulse power generator to various alarm applications. In FIG. 1 for example, The spring 14 could be eliminated by using a flexible lever arm 8. Rod 17 and stops 19 could be eliminated by restricting the movement of hinge 12 or by putting a cap over cylinder 5. Spring 15 could be eliminated by using a clamp instead of hinge 12 to connect the lever arm 8 to support 13 and relying on the flexibility of lever arm 8 for the restoring force. FIGS. 1B and 1C show an embodiment where one piece of spring steel replaces all springs and the door bracket. FIG. 1B represents a closed door position and FIG. 1C represents an open door position.

Other mechanical arrangements could be used to adapt the pulse power generator to outward opening doors, windows, drawers, or any similar opening portal. Bracket 1 could be attached by a variety of fasteners to the door, or to other alarm installations.

Figure 9A:
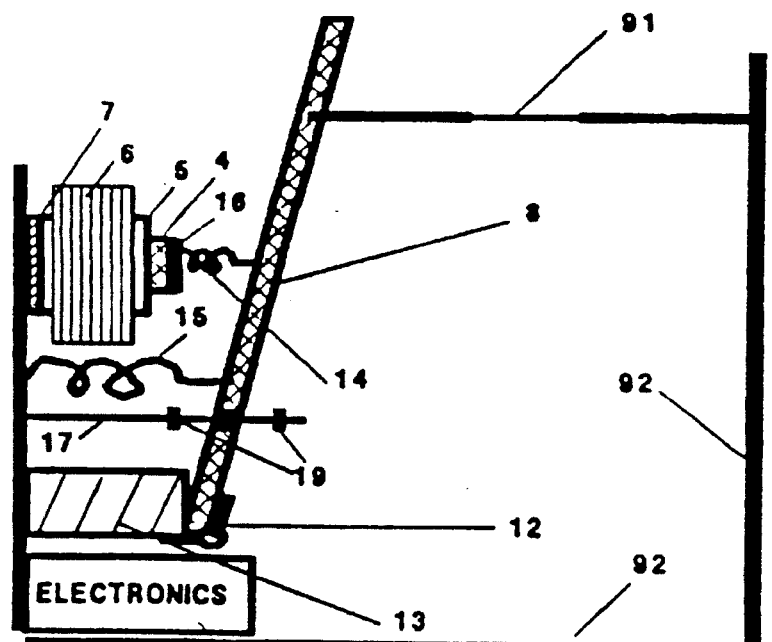
FIG. 9A is an embodiment using the pulse power generator as a heat sensitive fire alarm.

The pulse power generator described herein could also be adapted to a variety of uses other than alarms which could use mechanical energy inputs to power battery-less devices. For example, a fire alarm could be constructed by using a heat sensitive fusible arm to restrain the magnetic force wanting to produce a "jerk action" upon melting of the fusible link. FIG. 9A illustrates such an embodiment. In this embodiment, a configuration similar to FIG. 1 is used, but the lever arm 8 is restrained from releasing magnet 4 into coil 6 by a temperature sensitive fusible link 91.

Fusible link 91 is attached to support bracket 92. Electronics package 18 is shielded inside a fire resistant housing, and magnet 4 would probably use Samarium-Cobalt material to resist temperature weakening of the magnet. The fusible link 91 provides a one-way, one-time fire warning. For subsequent uses the fusible link would be replaced. For repeated use, fusible link 91 could be replaced by bimetallic, resetable linkages. The fire alarm could also be configured in the inverse manner, that is, with the magnet nominally inside the coil, and pulled out with a jerk when the temperature rises. This could be done with Nitinol (memory metal) wire springs, (or materials which shrink with temperature) used in place of fusible link 91.

Figure 9B:
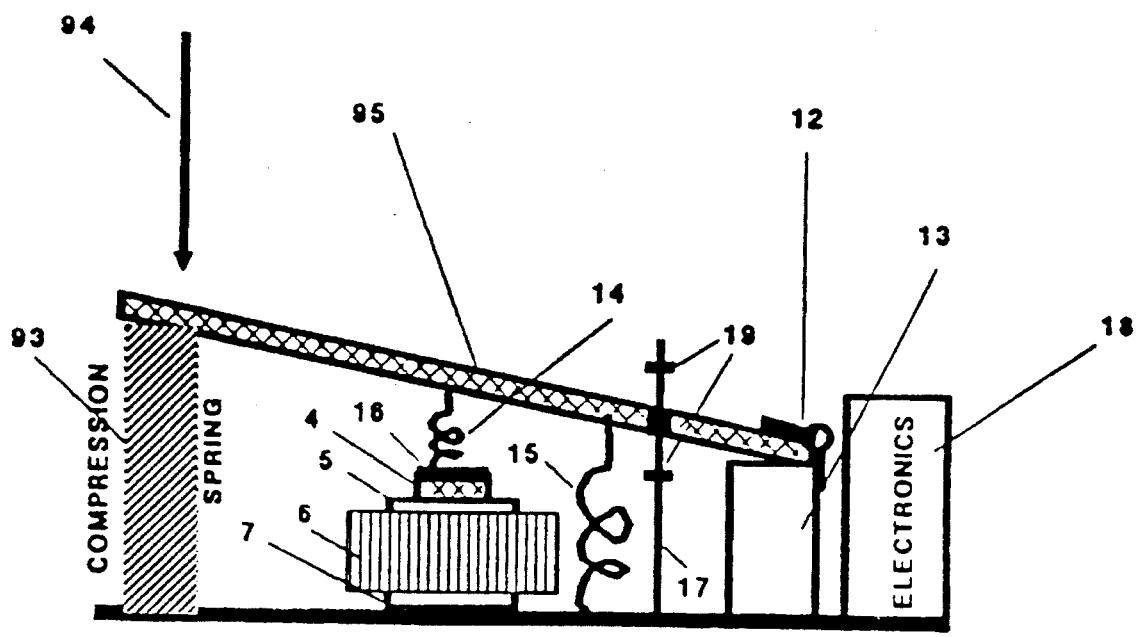
FIG. 9B is an embodiment using the pulse power generator as a sensor of people or vehicles on a platform.

A weight operated sensor could be constructed by using a configuration similar to FIG. 1, but replacing lever arm 8 with a platform 95 and adding a compression spring 93 to lift platform 95 and magnet 4 out of coil 6 when a weight 94 is applied. FIG. 9B illustrates one such embodiment. Platform 95 could also be made level with multiple compression springs 93 used to position the platform 95 in the nominal position in which it holds the magnet 4 outside the coil 6. Such a weight operated sensor could provide remote warning or counting of people, animals, or vehicles treading over the platform, count barrels rolled over the platform, etc. The weight operated sensor would again never need battery replacement, and would be capable of radiating wireless information to a remote control station.

Having thus described the present invention by way of practical examples thereof, modifications whereof will be apparent to those skilled in the art, what is claimed is as follows:

I claim:

1. A pulse power generator for generating an electrical pulse from mechanical energy comprising:

a coil of conductive wire, a rare earth magnet positioned to produce lines of magnetic flux passing through said coil, a jerk action means for assuring that at least a portion of said mechanical energy is expressed in jerking motions which are:

sometimes in a first direction causing a rapid change in the distribution of said lines of magnetic flux and a voltage pulse in said coil, defining a first pulse shape and sometimes in a second direction causing rapid changes in the distribution of said lines of magnetic flux and a voltage pulse in said coil defining a second pulse shape substantially different from said first pulse shape, a pulse shaping circuit means electrically connected to said coil for shaping the pulses produced by said jerking motions said pulses having a peak power of at least 0.1 Watt, a duration of at least 30 milliseconds and at least 0,001 joules of electrical energy.

2. A pulse power generator as in claim 1 wherein said pulse shape has a polarity dependent upon the direction of said jerking motion.

3. A pulse power generator as in claim 1 wherein said rare earth magnet is movably positioned at least partially inside said coil.

4. A pulse power generator as in claim 1 wherein said rare earth magnet is stationary and further comprising permeable pole pieces attached to said magnet and positioned to change the magnetic flux path flowing inside said coil upon the occurrence of said jerking action.

5. A pulse power generator as in claim 1 wherein one of said jerking motions is triggered by higher than normal temperature.

6. A pulse power generator as in claim 1 and further comprising a platform and a compression spring supporting said platform wherein one of said jerking motions is triggered by the weight of objects or people on said platform.

7. A battery-less alarm device comprising:

(a) a pulse power generator for generating electrical pulses from mechanical energy comprising:

a coil of conductive wire, a rare earth magnet positioned to produce lines of magnetic flux passing through said coil, a jerk action means for assuring that at least a portion of said mechanical energy is expressed in jerking motions which are:

sometimes in a first direction causing a rapid change in the distribution of said lines of magnetic flux and a voltage pulse in said coil, defining a first pulse shape and sometimes in a second direction causing rapid changes in the distribution of said lines of magnetic flux and a voltage pulse in said coil defining a second pulse shape substantially different from said first pulse shape, a pulse shaping circuit means electrically connected to said coil for shaping the pulses produced by said jerking motions said pulses having a peak power of at least 0.1 Watt, a duration of at least 30 milliseconds, and at least 0.001 joules of electrical energy, and (b) a transmitter means for transmitting a radio signal upon the occurrence of said jerking motion.

8. A pulse power generator as in claim 7 and further comprising a coding means for indicating the direction of said jerking.

9. An alarm device as in claim 8 wherein said coding means is also for indicating the identity of said pulse power generator.

10. An alarm system comprising:
(a) a pulse power generator for generating an electrical pulse from mechanical energy comprising:
  a coil of conductive wire,
  a rare earth magnet positioned to produce lines of magnetic flux passing through said coil,
  a jerk action means for assuring that at least a portion of said mechanical energy is expressed in a jerking motion which is sometimes in a first direction and sometimes in a second direction so as to cause in either case a rapid change in the distribution of said lines of magnetic flux,
  a pulse shaping circuit means electrically connected to said coil for producing an electrical pulse from said rapid change in the distribution of said lines of flux, said pulse having a peak power of at least 0.1 Watt, a duration of at least 30 milliseconds, and at least 0,001 joules of electrical energy.
(b) a transmitter means for transmitting a radio signal upon the occurrence of said jerking motion, and
(c) a receiver means for receiving said radio signal.

11. An alarm system as in claim 10 and further comprising a coding means for indicating the direction of said jerking, and a decoder means for decoding said radio signal to determine the direction of said jerking motion based on said polarity.

12. An alarm system as in claim 11 and further comprising a decoder means for identifying the particular pulse generator device being activated.

13. An alarm device comprising:
(a) a pulse power generator for generating electrical pulses from mechanical energy comprising:
  a coil of conductive wire,
  a rare earth magnet positioned to produce lines of magnetic flux passing through said coil,
  a jerk action means for assuring that at least a portion of said mechanical energy is expressed in jerking motions which are:
  sometimes in a first direction causing a rapid change in the distribution of said lines of magnetic flux and a voltage pulse in said coil, defining a first pulse shape and
  sometimes in a second direction causing rapid changes in the distribution of said lines of magnetic flux and a voltage pulse in said coil defining a second pulse shape substantially different from said first pulse shape,
  a pulse shaping circuit means electrically connected to said coil for shaping the pulses produced by said jerking motions said pulses having a peak power of at least 0.1 Watt, a duration of at least 30 milliseconds, and at least 0,001 joules of electrical energy, and
(b) a transmitter means for transmitting a radio signal upon the occurrence of said jerking motions, and
(c) a receiver means for receiving said radio signal.

* * * * *